June 28, 1960 J. R. STETLER Plant Pat. 1,955
PEACH TREE
Filed Sept. 22, 1959
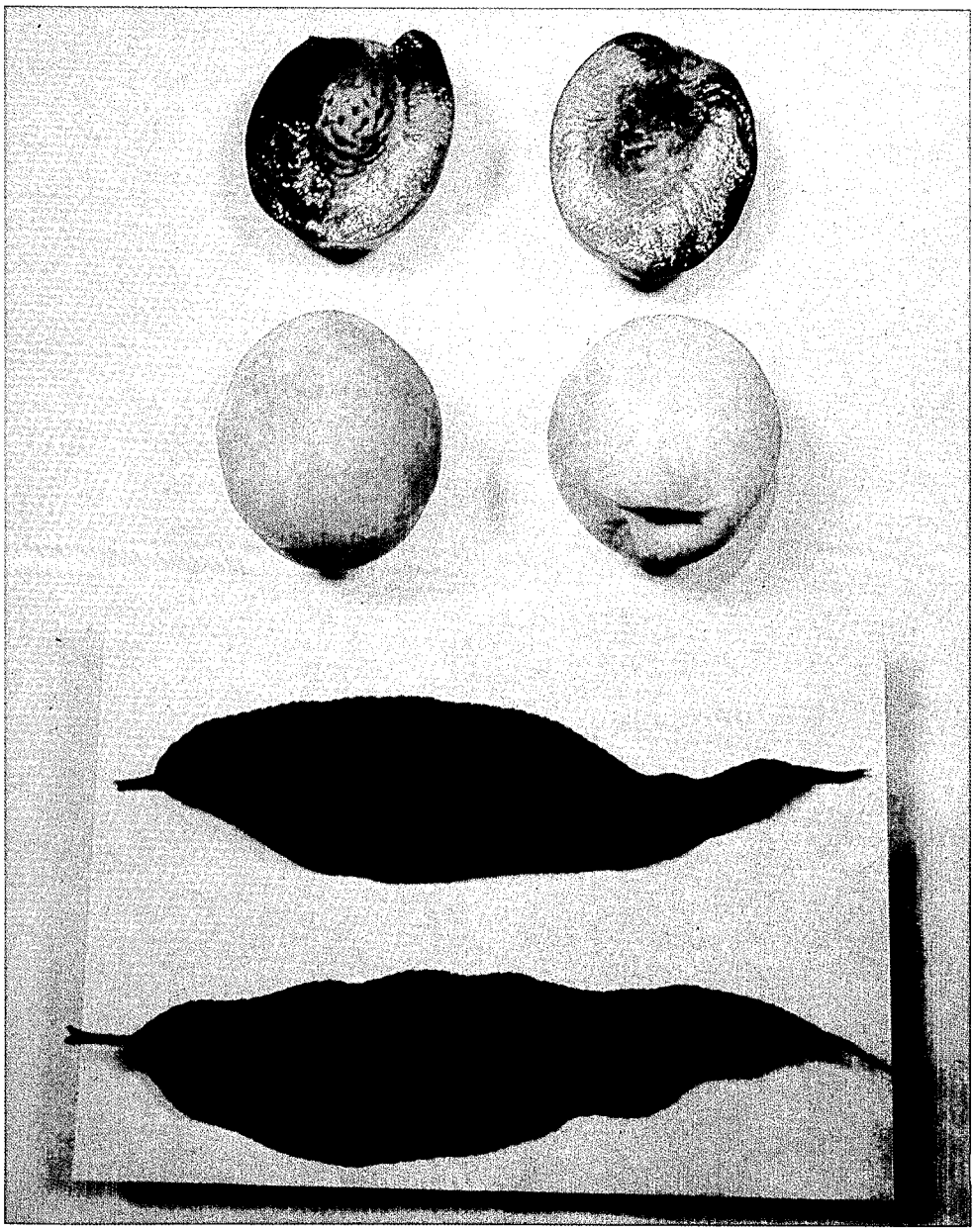
INVENTOR
J. R. Stetler
BY Robb & Robb
ATTORNEYS United States Patent Office Plant Pat. 1,955
Patented June 28, 1960

1,955

PEACH TREE

James Robert Stetler, Ashfield, Pa., assignor to Edgar H. Kemp and Homer S. Kemp, trading as Bountiful Ridge Nurseries, Princess Anne, Md., copartners Filed Sept. 22, 1959, Ser. No. 841,660

1 Claim. (Cl. 47—62)

The present invention relates to a new and distinct variety of peach tree which was discovered by me on my cultivated property near Ashfield, in the County of Carbon, Pennsylvania, as a newly found seedling.

At the time of my initial discovery of the new peach seedling, I had been growing in the garden on my farm near Ashfield, Pennsylvania a number of different varieties of peach trees, including "Red Haven," "Golden Jubilee," "Belle of Georgia," and "Elberta," all unpatented, and it had been my practice for many years to "put up" substantial quantities of the fruit, as by canning, preserving, etc. When engaged in the canning and preserving operations, it was my general practice to discard the seeds, and other waste by depositing the same in my garden area on the farm, and apparently as the result of this, a number of seedlings grew up in this area, one of which was discovered by me near the edge of the garden in close proximity to a cherry tree. Except for this latter seedling, the others were cut down and destroyed in order to avoid undue interference with cultivation of the garden. Since the one near the cherry tree was not in the way, it was allowed to grow, and as it developed, it began to bear fruit which appeared to be interesting and rather unique. Accordingly, the cherry tree was pruned away in order to allow more room for the peach tree, and the peach tree was carefully preserved and kept under observation. Later, I asexually reproduced the same by budding and had other plants propagated on my behalf by budding, the latter being grown in Princess Anne, Somerset County, Maryland.

Continued observations of the original seedling, as well as the asexually reproduced plants, conclusively showed that these trees were new and distinct varieties, evidently originating from open-pollenation of one of the varieties formerly being grown by me, but from which the new variety was clearly differentiated, as well as from all other varieties of which I am aware, as evidenced by the following unique combination of characteristics which are outstanding in the new variety:

(1) An exceptionally vigorous habit of growth;
(2) Good hardiness;
(3) Good disease resistance;
(4) Good productivity;
(5) Self-fertility;
(6) An unusually early fruit-bearing habit;
(7) A very high fruit color (good Golden Yellow, almost entirely covered with Brilliant Red);
(8) An unusually early fruit-ripening habit;
(9) Large fruit size;
(10) Good flavor of the fruit; and
(11) Good shipping and storage qualities of the fruit.

In comparison with other varieties, the fruit of my new variety somewhat resembles that of "Red Haven" from a color viewpoint, but more closely resembles "Golden Jubilee" in shape. However, the fruit is definitely distinguishable from both of these varities, and to the best of my belief, ripens much earlier than any prior yellow freestone peach. For example, the fruit of the new variety ripens about 10 days after that of the variety "Redwin" (Plant Patent No. 1,661), at least several days before the fruit of the variety "Cardinal" (unpatented), about 10 days earlied than "Erly-Red-Fre" (Plant Patent No. 320), and at least 20 days earlier than "Red Haven" (unpatented).

Asexual reproduction of my new variety by budding, as performed at Ashfield, Pennsylvania, and also at Princess Anne, Maryland, shows that the foregoing characteristics and distinctions come true to form and are established and transmitted through succeeding propagations.

The accompanying drawing shows typical specimens of the foliage and fruit of my new variety as depicted in color as nearly true as it is reasonably possible to make the same in a color illustration of this character, said fruit being shown in elevation and also in cross-section, with one half-section exposing the cavity and the other half-section exposing the stone seated in the cavity, and the foliage specimens depicting both the upper and under surfaces of typical leaves.

The following is a detailed description of the new variety, with color terminology in accordance with Maerz and Paul Dictionary of Color, except where general color terms of ordinary dictionary significance are obvious:

(Observations made from specimens grown at Princess Anne, Maryland.)

Dates first and last picking: About June 26 and June 30, respectively.

Tree: Large; vigorous; upright; dense; round-topped; hardy; productive; regular bearer.

*Trunk.*—Stocky; medium smoothness.

*Branches.*—Stocky; smooth; glossy. Color—1-year wood—Titian, Plate 13, Color J–12; old wood—Brown, Plate 14, Color G–8. Lenticles—medium number; medium size.

*Leaves.*—Medium thickness; smooth. Size—large; length—from 7 to 7¾ inches; width—from 1½ to 2 inches. Shape—oval, lanceolate; acutely pointed. Color—upper side—Cedar Green, Plate 23, Color L–5; under side—Green, Plate 23, Color L–2. Margin—crenate; coarsely serrate. Petiole—medium thickness. Glands—usually 2 on one side and 1 on the other, opposite, medium size, reniform, located at the base of the leaf; color—green. Stipules—none.

Flower buds: Hardy; large; long; plump; free; very slight pubesence.

Flowers: Dates of first and full bloom—about April 2 and April 5, respectively; medium earliness.

*Size.*—Medium.

*Color.*—Pink, Plate 1, Color C–1.

Fruit: Maturity when described—Eating-ripe. Date—June 30.

*Size.*—Medium. Axial diameter—about 2⅜ inches. Transverse diameter in suture plane—about 2⅛ inches. Diameter at right angles to suture plane—about 2 inches.

*Form.*—Uniform; symmetrical; oblong; narrowly ovoid; compressed laterally toward suture.

*Suture.*—An inconspicuous line; shallow; extends from base; has slight depression beyond pistil point.

*Ventral surface.*—Rounded; lipped toward apex throughout both sides; lips equal.

*Cavity.*—Abrupt; elongated in suture plane, with suture showing on both sides. Depth—from about ⅜ inch to about ½ inch. Breadth—from about ½ inch to about ⅝ inch. Markings—none.

*Base.*—Rounded.

*Apex.*—Short; mammiform; rounded; oblique pistil point.

*Stem.*—Medium thickness; glabrous; strong adherence to stone. Length—from about ⅜ inch to about ½ inch.

*Skin.*—Medium thickness; medium toughness; astringent; free; no tendency to crack in dry season. Color—Cadmium Y P, Plate 9, Color L–8, covered almost entirely with Flash Red, Plate 3, Color K–11. Down—scant; short; does not roll up when rubbed.

*Flesh.*—Color—yellow, streaked with red throughout.

*Surface of pit cavity.*—Color—yellow, with pale yellow fibres.

*Amydgalin.*—Wanting.

*Juice.*—Abundant; rich.

*Texture.*—Firm; fine; meaty; melting.

*Fibers.*—Few, fine; tender.

*Ripens.*—Evenly.

*Flavor.*—Subacid; mild.

*Aroma.*—Distinct.

*Eating quality.*—Good.

Stone: Free; parts from flesh smoothly, but retains short fibre-like threads along ridges.

*Size.* — Small. Length — about 1½ inches. Breadth—about ⅞ inch. Thickness—about 9/16 inch.

*Form.*—Elliptical.

*Base.*—Straight.

*Hilum.*—Narrow; oval.

*Apex.*—Acute.

*Sides.*—Unequal; curved on right side.

*Surface.*—Regularly furrowed near base toward apex; ridged near base toward apex; pitted throughout.

*Ridges.*—Rounded toward base.

*Pits.*—Elongated.

*Ventral edge.*—Thin; with wing toward base.

*Dorsal edge.*—Narrow; with shallow, narrow groove toward base.

*Ridges on either side.*—Interrupted.

Disease resistance: Good resistance to fungus diseases such as bacteriosis (bacterial spot), mildew, brown rot and stricture canker, as determined from comparison with other varieties grown under comparable cultural conditions at Princess Anne, Maryland.

Insect resistance: Good resistance to Oriental moth, curculia, and coddling moth, as determined from comparison with other varieties grown under comparable cultural conditions at Princess Anne, Maryland.

Use: Market; local; dessert; culinary; canning.

Keeping quality: Good.

Shipping quality: Good.

I claim:

A new and distinct variety of peach tree of the yellow freestone fruit-bearing class, substantially as herein shown and described, characterized particularly as to novelty by the unique combination of an exceptionally vigorous habit of growth, good hardiness, good disease resistance, self-fertility, good fruit productivity, an unusually early fruit-bearing habit, a very high fruit color of good Golden Yellow almost entirely covered with Brilliant Red, an unusually early fruit-ripening habit, large fruit size and good flavor, and good shipping and storage qualities of the fruit.

No references cited.